(12) United States Patent
Liu et al.

(10) Patent No.: US 9,194,797 B2
(45) Date of Patent: Nov. 24, 2015

(54) METHOD AND SYSTEM FOR DETECTING MOISTURE IN A PROCESS GAS INVOLVING CROSS INTERFERENCE

(71) Applicant: General Electric Company, Schenectady, NY (US)

(72) Inventors: Xiaoyong Frank Liu, Wellesley, MA (US); Yufeng Huang, Andover, MA (US); Gary S. Parece, Belmont, MA (US); Anthony Kowal, Berlin, MA (US); Chong Tao, Winchester, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/137,160

(22) Filed: Dec. 20, 2013

(65) Prior Publication Data

US 2015/0177131 A1    Jun. 25, 2015

(51) Int. Cl.
| | |
|---|---|
| *G01N 21/00* | (2006.01) |
| *G01N 21/39* | (2006.01) |
| *G01N 21/59* | (2006.01) |
| *G01N 21/88* | (2006.01) |
| *G01N 33/00* | (2006.01) |
| *G01N 21/3504* | (2014.01) |
| *G01N 21/3554* | (2014.01) |

(52) U.S. Cl.
CPC ............ *G01N 21/39* (2013.01); *G01N 21/3504* (2013.01); *G01N 21/3554* (2013.01); *G01N 21/59* (2013.01); *G01N 21/8806* (2013.01); *G01N 33/0016* (2013.01); *G01N 33/0047* (2013.01); *G01N 33/0062* (2013.01); *G01N 2021/399* (2013.01); *G01N 2201/0612* (2013.01)

(58) Field of Classification Search
USPC ........ 356/432–444; 250/339.12, 339.13, 343; 422/83; 73/23.34, 2, 29.01
See application file for complete search history.

(56) References Cited

U.S. PATENT DOCUMENTS

| | | | |
|---|---|---|---|
| 3,979,589 | A | 9/1976 | Sternberg et al. |
| 4,589,971 | A | 5/1986 | Mayeaux |
| 5,821,537 | A | 10/1998 | Ishihara et al. |
| 6,353,225 | B1 | 3/2002 | Strzoda et al. |
| 6,519,039 | B1 | 2/2003 | Morishita et al. |
| 6,552,792 | B1 | 4/2003 | Pilgrim et al. |

(Continued)

FOREIGN PATENT DOCUMENTS

| | | |
|---|---|---|
| EP | 1860425 A1 | 11/2007 |
| GB | 2466181 A | 6/2010 |

(Continued)

OTHER PUBLICATIONS

International Search Report and Written Opinion issued in connection with corresponding PCT Application No. PCT/US2014/070839 dated Mar. 11, 2015.

*Primary Examiner* — Tri T Ton
(74) *Attorney, Agent, or Firm* — Fletcher Yoder P.C.

(57) ABSTRACT

A system includes a moisture analyzer configured to detect moisture in a process gas. The moisture analyzer includes an absorption cell that encloses and conducts the process gas. The moisture analyzer also includes a pressure control device that may reduce a pressure of the process gas inside the absorption cell. The moisture analyzer includes a light emitting device that may transmit light through the process gas inside the absorption cell, as well as a photodetector that may detect an intensity of the light transmitted through the process gas and exiting the absorption cell.

20 Claims, 5 Drawing Sheets

(56) References Cited

U.S. PATENT DOCUMENTS

| | | |
|---|---|---|
| 6,657,198 B1 | 12/2003 | May |
| 6,775,001 B2 | 8/2004 | Friberg et al. |
| 7,064,329 B2 | 6/2006 | Webber |
| 7,502,115 B2 | 3/2009 | Patel et al. |
| 7,586,094 B2 | 9/2009 | Liu et al. |
| 7,679,059 B2 | 3/2010 | Zhou |
| 7,728,978 B2 | 6/2010 | Zhou et al. |
| 2003/0080295 A1 | 5/2003 | Webber et al. |
| 2006/0263256 A1 | 11/2006 | Koshel et al. |
| 2007/0081162 A1 | 4/2007 | Roller et al. |
| 2008/0255769 A1 | 10/2008 | Zhou et al. |
| 2010/0089117 A1 | 4/2010 | Liu et al. |
| 2010/0091278 A1 | 4/2010 | Liu et al. |
| 2010/0180667 A1 | 7/2010 | Bender et al. |

FOREIGN PATENT DOCUMENTS

| | | |
|---|---|---|
| GB | 2493833 A | 2/2013 |
| JP | 2002131228 A | 5/2005 |
| WO | 2005047872 A1 | 5/2005 |

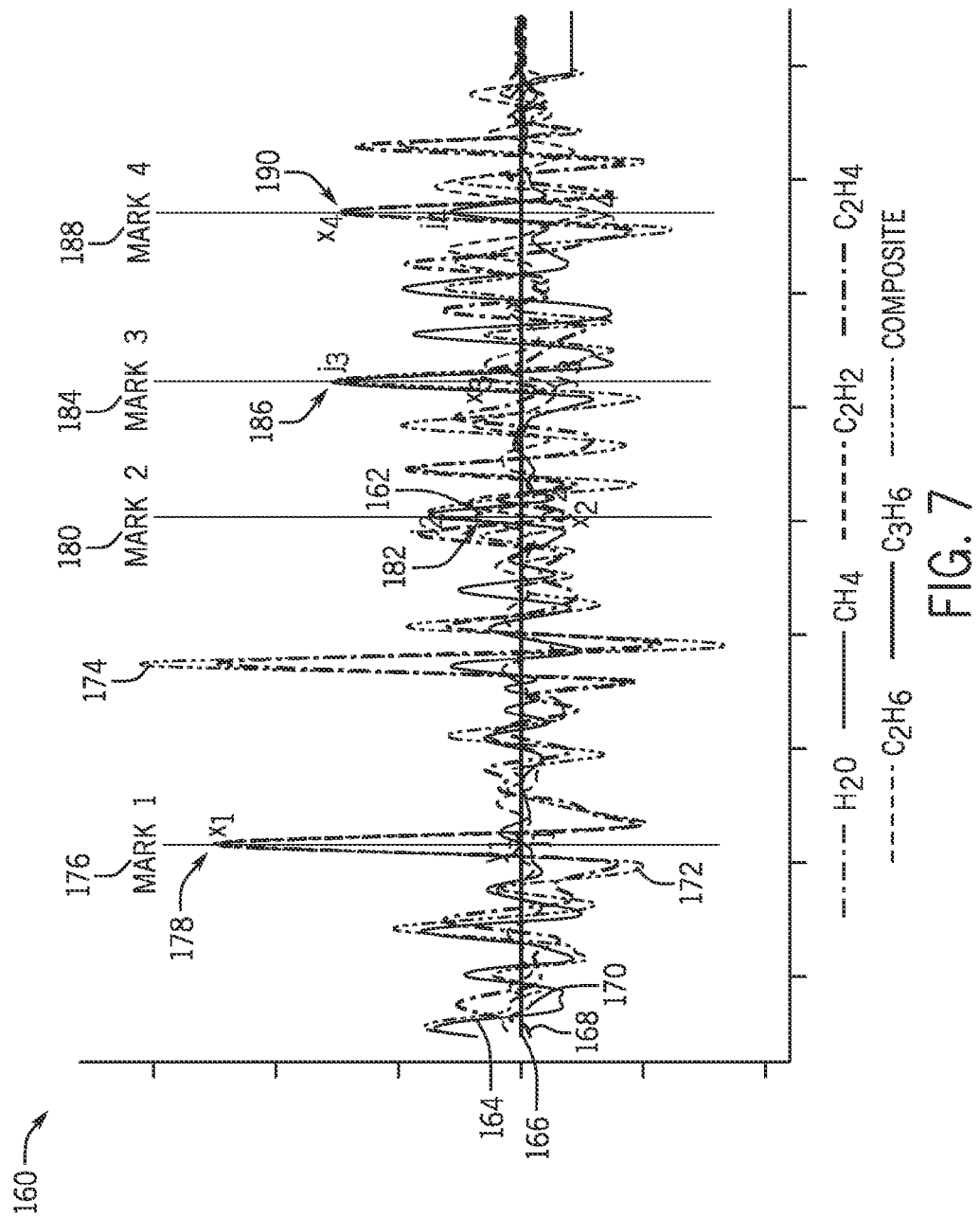

METHOD AND SYSTEM FOR DETECTING MOISTURE IN A PROCESS GAS INVOLVING CROSS INTERFERENCE

BACKGROUND OF THE INVENTION

The subject matter disclosed herein relates generally to spectroscopy, and more particularly, to absorption spectroscopy for detection of moisture in a process gas involving cross interference. Examples of process gases include, but are not limited to, natural gas, cracked gas out of a steam cracker, polyethylene feedstock, and hydrogen recycle gas.

Absorption spectroscopy based moisture analyzers exist for determining moisture concentration in a sample gas. However, determination of the concentration of moisture (i.e., water vapor), in a process gas may be complicated. For example, spectral interference between moisture and background gas (i.e., the process gas minus moisture) may be severe enough to pose a challenge to achieve desired sensitivity or accuracy in determining the concentration of moisture in the process gas.

Differential spectroscopy may be employed to reduce the spectral interference from background gas to determine the concentration of moisture in a process gas. One example of a process used in differential spectroscopy may include recording a spectrum of the background gas, which is essentially dried process gas, subtracting this spectrum from a spectrum of the process gas to yield a differential spectrum, and determining the moisture concentration based upon the differential spectrum. However, this process requires a gas purifier and other requisite accessories to remove moisture from the process gas to record the background spectrum, which may be costly. Additionally, this process requires a switch between the sample gas to be analyzed (i.e., the process gas) and the reference gas (i.e., gas dried by the purifier, which is representative of the background gas), which may slow the system response time.

Moreover, there is no guarantee that the spectral interference would be effectively removed because the spectra of the sample gas and the background gas are not recorded at the same time and/or the chemical composition of background gas may vary over time, and, thus, its spectrum may vary over time.

Further, a process gas can vary in temperature, pressure, and composition. These variations may cause a calibration drift in tunable diode laser absorption spectroscopy (TDLAS) based moisture analysis, because the gas sample used for calibration of the equipment may not account for these variations. Accordingly, an approach that adequately addresses present issues regarding detecting moisture in a process gas is desirable.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a system includes a moisture analyzer configured to detect moisture in a process gas, which includes an absorption cell enclosing and conducting the process gas, a pressure control device configured to reduce a pressure of the natural gas inside the absorption cell, a light emitting device configured to transmit light through the process gas inside the absorption cell, and a photodetector configured to detect an intensity of the light transmitted through the process gas and exiting the absorption cell.

In another embodiment, a method includes reducing a pressure of process gas by a pressure control device to generate de-pressurized process gas at a pressure lower than an ambient pressure of the process gas, transmitting a light through the de-pressurized process gas at a pre-selected wavelength or across a wavelength range, recording a spectrum of the de-pressurized process gas, and determining a concentration of moisture in the process gas based on the spectrum of the process gas.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 7 is a diagram illustrating spectral data representative of a cracked gas mixture typically having $CH_4$, $C_2H_4$, and $C_2H_6$ in relatively high percentages, $C_2H_2$ and $C_3H_6$ in relatively low percentage, and trace level moisture ($H_2O$), in accordance with an embodiment.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed below, the disclosed embodiments relate to the application of a spectral linewidth reduction method, and a system based on such a method, to improve the detection of moisture in a process gas, including but not limited to pipeline natural gas, LNG (liquefied natural gas) feed gas, regasified LNG, cracked gas out of a steam cracker, polyethylene feedstock, and hydrogen recycle gas. The system and method may also eliminate or reduce the spectral interference from background gas (i.e., dried process gas) when detecting moisture in the process gas. In particular, the disclosed embodiments reduce sample gas pressure to reduce the overall spectral linewidth for a sample gas. This reduction in the overall spectral linewidth for a sample gas lowers background gas interference and enables more sensitive and more accurate detection of moisture in a process gas. That is, the disclosed embodiments reduce a sample gas pressure without having to compromise on response time, or deconvolute moisture and background gas absorption, since a single spectrum of a process gas sample may be utilized to determine the concentration of moisture in the process gas sample.

Figure 1:
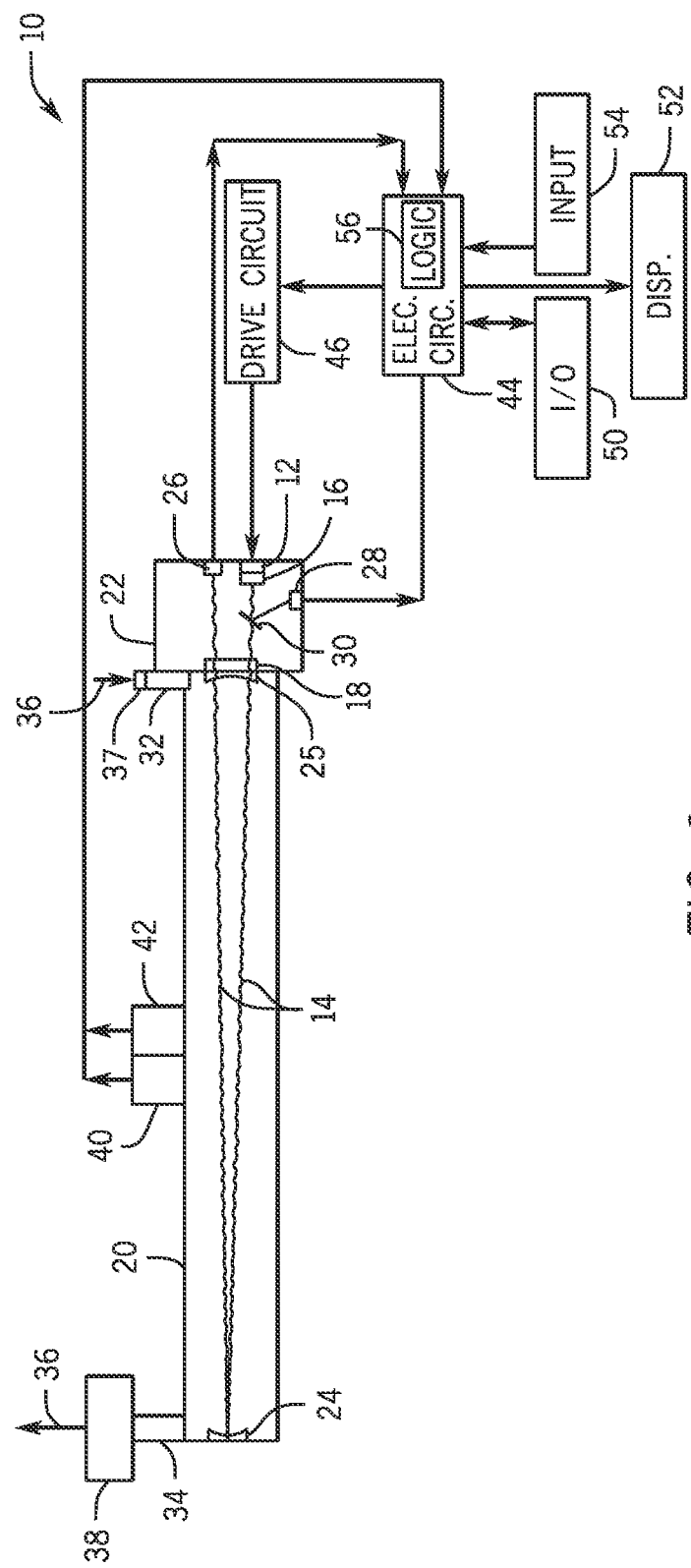
FIG. 1 is a block diagram of a tunable diode laser absorption spectrometer in accordance with an embodiment of the present technique.

Turning now to the drawings and referring first to FIG. 1, an embodiment of a wavelength-modulation spectroscopy analyzer 10 is illustrated. This analyzer 10 may generally detect moisture in a gas, such as natural gas. The analyzer may include, for example, a light emitting device 12. The light emitting device 12 may include, for example, a laser, a diode laser, a quantum cascade laser, or another light source. The light emitting device 12 may emit, for example, light at one or more particular wavelengths and at one or more particular modulation frequencies, which may be determined, for example, by a user. In one embodiment, the light emitting device 12 is a laser and may operate to transmit light at a single wavelength at a time. In another embodiment, the wavelength can be swept across a certain range and modulated at a certain frequency.

The light emitted by the light emitting device 12 may include a monochromatic radiation 14 that may pass through a collimator 16 that operates to collimate the monochromatic radiation 14. The collimated monochromatic radiation 14 may be transmitted to and through an optical window 18, so that the monochromatic radiation 14 may be transmitted into an absorption cell 20 (e.g., an enclosure). In this manner, monochromatic radiation 14 may pass from a chamber 22 into the absorption cell 20 while gases present, for example, in the absorption cell 20, may be prevented from entering the chamber 22.

In one embodiment, the absorption cell 20 may be a multipass absorption cell that enables the monochromatic radiation 14 to be reflected between a reflective element 24 (e.g., a mirror) at one end of the absorption cell 20 opposite of the window 18, and another reflective element 25 (e.g., a second mirror) at the other end of the absorption cell 20, before exiting the absorption cell 20 through the window 18 and into the chamber 22. The monochromatic radiation 14 may then be detected by a photodetector 26. In this manner, the photodetector 26 may operate to detect an intensity of monochromatic radiation 14 exiting the absorption cell 20. In one embodiment, the light emitting device 12 may be provided by a laser diode integrated with a thermoelectric cooler (TEC), a temperature sensor, and a built-in photodetector that can detect the intensity of backward emission from the laser diode.

In another embodiment, an external reference photodetector 28 can be employed in addition to, or instead of, the built-in photodetector. As illustrated in FIG. 1, a beam splitter 30 may be utilized to split the monochromatic radiation 14. The beam splitter 30 may receive the monochromatic radiation 14 and may direct a portion of the monochromatic radiation 14 to the reference photodetector 28, and may enable the rest of the monochromatic radiation 14 to transmit through the absorption cell 20. In one embodiment, use of the reference photodetector 28 may be desirable in spectroscopy applications where a light emitting device 12 with a built-in photodetector is not readily available for a desired monochromatic radiation wavelength, where an external reference photodetector 28 is preferred, or where it is desirable to monitor the concentration of an analyte leaking into the chamber 22.

Additionally, the analyzer 10 may include a gas inlet 32 and a gas outlet 34 coupled to the absorption cell 20. The inlet 32 may operate to conduct a gas flow 36 into the absorption cell 20, while the outlet may operate to conduct the gas flow 36 out of the absorption cell 20. In one embodiment, this gas flow 36 may include a process gas. The gas flow 36 may be pipeline natural gas, LNG feed gas, regasified LNG, cracked gas out of a steam cracker, polyethylene feedstock, or hydrogen recycle gas. The inlet 32 may receive the gas flow 36 and may transmit the gas flow 36 into the absorption cell 20, where the gas flow 36 may be analyzed for moisture content. Additionally, the gas flow 36 may be de-pressurized by a pressure control device 38 downstream of an outlet 34 to enable more sensitive and more accurate detection of moisture in the process gas.

The pressure control device 38 may be, for example, a vacuum pump, an aspirator, or another de-pressurizing device, which may operate to reduce the pressure of the gas flow 36 from, for example, one standard atmosphere to a pressure substantially lower than one standard atmosphere (e.g., near one trillionth ($10^{-12}$) of atmospheric pressure), with assistance from a gas flow limiting device 37 upstream of the inlet 32. The gas flow limiting device 37 may include any flow restrictor or regulator able to restrict the gas flow 36, such as a venturi section (e.g., converging passage, throat, and then diverging passage) or an orifice with a diameter less than the diameter of a conduit used to conduct gas flow 36. The pressure control device 38 may reduce the pressure of the gas flow 36 to approximately, 8 psia (pounds per square inch absolute), 7.5 psia, 7 psia, 6.5 psia, 6 psia, 5.5 psia, 5 psia, 4.5 psia, 4 psia, 3.5 psia, 3 psia, 2.5 psia, 2 psia, 1.5 psia, 1 psia, or 0.5 psia or between approximately 1 psia and 5 psia.

The analyzer 10 may also include one or more sensors, such as a pressure sensor 40 and/or a temperature sensor 42. The pressure sensor 40 may acquire pressure measurements of the gas flow 36, while the temperature sensor 42 may acquire temperature measurements of the gas flow 36. These measurements may be provided to electronic circuitry 44. The electronic circuitry 44 may include one or more processors that may be digital signal processors, microprocessors, field-programmable gate arrays, complex programmable logic devices, application specific integrated circuits, and/or other logic circuitry. The electronic circuitry 44 may receive signals from the photodetector 26, the reference photodetector built into the light emitting device 12 (and/or the external reference photodetector 28), the pressure sensor 40, and the temperature sensor 42. The electronic circuitry 44 may utilize these signals to analyze and determine analyte concentration in the gas flow 36, such as the concentration of moisture in, for example, natural gas, based on the measured spectrum, pressure, and temperature of the gas flow 36. Additionally, the electronic circuitry 44 may also command a drive circuit 46 of the light emitting device 12. In one embodiment, the analyzer 10 may further include a display 52, an input device 54, and one or more I/O interfaces 50.

In one embodiment, the analyzer 10 may utilize absorption spectroscopy to determine the concentration of moisture of in the gas flow 36. The methods of absorption spectroscopy may include, but are not limited to, direct absorption spectroscopy, harmonic/derivative spectroscopy, photoacoustic spectroscopy, cavity ring down spectroscopy, and fluorescence spectroscopy.

Spectral interference between, for example, moisture and the background gas in the gas flow 36, may be primarily caused by coincidental yet inherent adjacency between the transition frequencies of moisture and the background gas. However, the wavelength of the monochromatic radiation 14 emitted by the light emitting device 12 may be chosen to avoid such coincidental adjacency and minimize the spectral interference from the background gas. Moreover, through the use of the gas flow limiting device 37 and the pressure control device 38, the pressure of the gas flow 36 may be reduced, leading to reduced spectral line width and, thus, reduced spectral interference between, moisture and the background gas in the gas flow 36.

In certain embodiments, the electronic circuitry 44 or a separate computer processor may implement logic 56 to account for extensive cross interference between moisture and the background gas, the composition of which can be constant or more often, variable. As mentioned above, based upon variances in sample temperature, pressure, and composition, the calibration of the analyzer 10 may drift, thus reducing accuracy of the analyzer 10. As will be discussed in more detail below, by incorporating the logic 56, the analyzer 10 may have a reduced sensitivity to background gas effects caused by variances of the process gas.

Figure 2:
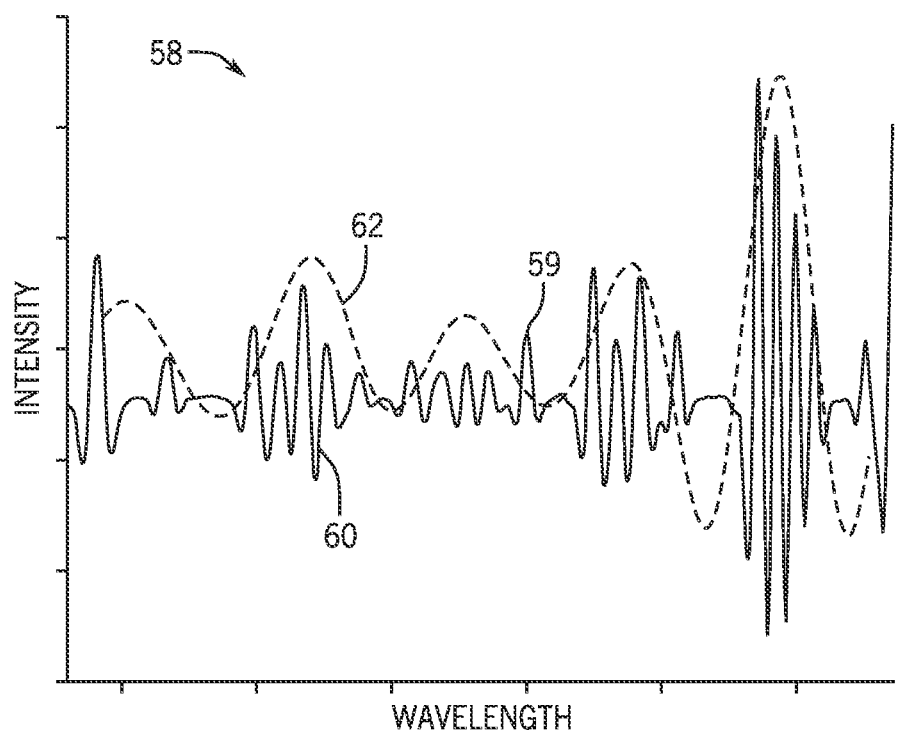
FIG. 2 is a chart illustrating of an example of a second harmonic spectrum of natural gas by a spectrometer of FIG. 1 in accordance with an embodiment of the present technique.

FIG. 2 illustrates a chart 58 that details a second harmonic (2f) spectrum 60 for a gas flow 36 (e.g., natural gas) at a reduced pressure (e.g., 2.5 psia, 5 psia, or 8 psia) containing a certain level of moisture content when exposed to the monochromatic radiation 14 across a range of wavelengths. Also illustrated in chart 58 is another 2f spectrum 62 for a gas flow 36 (e.g., natural gas) when exposed to the monochromatic radiation 14 across a range of wavelengths at an ambient pressure while containing the same level of moisture content as gas flow 36 at the reduced pressure (i.e., the same level of moisture content present in the gas flow 36 for the 2f spectrum 60). As illustrated in chart 58, at ambient pressure, the 2f spectrum 62 is poorly resolved due to line broadening along the wavelength axis, the spectral lines are clumped together, and the targeted spectral line of moisture 59 is barely visible. In contrast, the 2f spectrum 60 is well resolved along the wavelength axis, revealing fine details that would otherwise be missing, including the targeted moisture line 59. Thus, chart 58 illustrates that de-pressurizing the gas flow 36 may enable the analyzer 10 to attain superior detection selectivity, accuracy, and sensitivity for the detection of moisture present in the gas flow 36.

Figure 3:
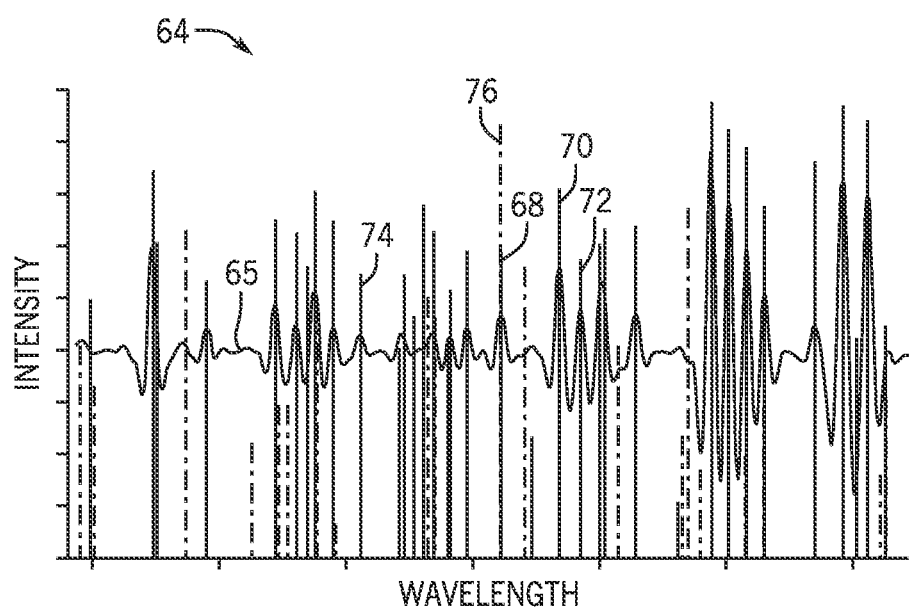
FIG. 3 is a chart illustrating of an example of another second harmonic spectrum of natural gas by a spectrometer of FIG. 1 in accordance with another embodiment of the present technique.

However meticulously the wavelength, or wavelength range, of a monochromatic radiation 14 is chosen, it is difficult to avoid altogether coincidental adjacency in spectral line positions, as the line positions are inherent and dictated by the molecular structures of species present in the gas flow 36. FIG. 3 illustrates a chart 64 that manifests such a difficulty. In chart 64, the smooth curve 65 illustrates a 2f spectrum of dry methane ($CH_4$) recorded at a reduced pressure (e.g., 2.5 psia, 5 psia, or 8 psia), the concentration of which is typically above 90% in natural gas. The solid straight lines in chart 64 are the spectral lines attributed to methane, including lines 68, 70, 72, and 74. The dashed straight lines in chart 64 are the spectral lines attributed to moisture, including the targeted line 76, which is used to detect moisture present in the gas flow 36.

As illustrated in chart 64, methane line 68 overlaps with moisture line 76 in wavelength. The ratio between methane line 68 and one or more of methane lines 70, 72 and 74 is spectroscopically inherent with methane, is a function of relative spectral intensity, gas pressure and temperature, and can be accurately calculated. In one embodiment, the analyzer 10 may be configured to calculate a methane baseline underlying the targeted moisture line, based on real-time detection of one or more of methane lines 70, 72, and 74, and based on a predetermined ratio between methane line 68 and one or more of methane lines 70, 72, and 74, 76, so that the methane baseline may be subtracted from a composite of the targeted moisture line 76 and the overlapping methane line 68, to determine the exact concentration of moisture in the gas flow 36.

Figure 4:
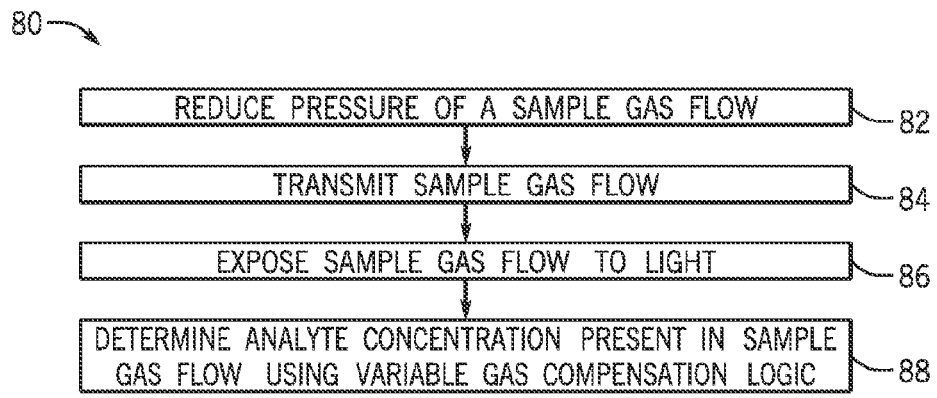
FIG. 4 is flow chart illustrating a process for performing spectral analysis with a spectrometer of FIG. 1 in accordance with an embodiment of the present technique.

FIG. 4 illustrates a flow chart 80 describing one embodiment for the detection of an analyte concentration in a gas flow 36, including, for example, a concentration of moisture in a process gas sample. In step 82, the pressure of the sample gas flow 36 may be reduced by, for example, a pressure control device 38 alone, or in combination with a flow limiting device 37. In step 84, the de-pressurized gas flow 36 is transmitted through an absorption cell 20. In step 86, the de-pressurized gas flow 36 is exposed to light from a light emitting device 12 inside the absorption cell 20. In step 88, the concentration of an analyte (e.g., moisture) in the sample gas flow (e.g., natural gas) is determined based on an absorption-based spectrum of the de-pressurized gas flow 36.

As discussed above, a process gas sample analyzed by tunable diode laser absorption spectroscopy (TDLAS) may vary in temperature, pressure, and composition. These variations in the gas samples may cause the calibration to drift, impacting the concentration determination of step 88. Accordingly, as part of step 88, the logic 56 may be implemented to counteract any background gas effects for the moisture analysis. As the logic 56 is able to compensate for a variable gas composition, the determined analyte concentration may become more accurate.

Figure 5:
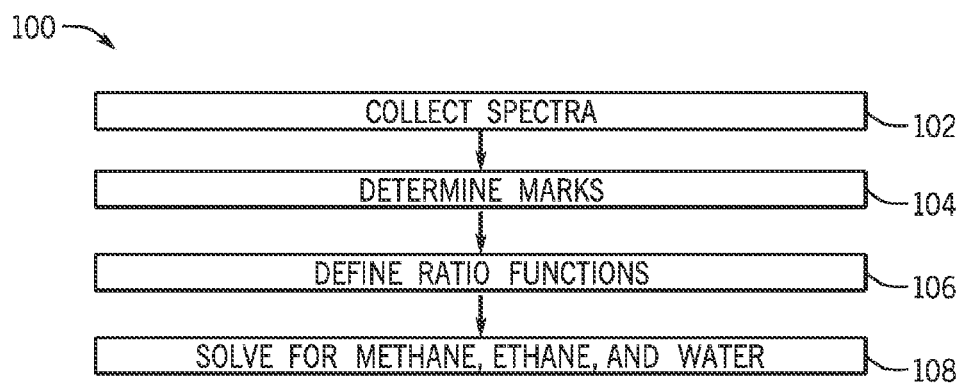
FIG. 5 is a flowchart illustrating a process for compensating for variable gas compositions in TDLAS, in accordance with an embodiment.

FIG. 5 illustrates a process 100 for compensating for variable gas compositions in TDLAS. First, spectral data for each of the interferents and moisture are collected (block 102). The spectral data may be collected with a TDLAS analyzer, at various sample pressures, for each of the interferents and moisture diluted in a non-interfering gas (e.g., $N_2$), logging pressure and temperature data among other things. The concentrations of the interferents should reflect the concentrations found in the actual process gas. In some embodiments, multiple spectra are collected and averaged to achieve a better accuracy.

Next, marks are defined within the spectral data (block 104). Variables are defined to represent the signal magnitude (Y value) at a certain index (X value) for each of the interferents and moisture as well as the process gas mixture. The number of marks defined within the spectral data is dependent on the number of interferents that may cause non-negligible interference. Specifically, the number of marks for the spectra data will be one more than the number of interferents that may cause non-negligible interference (# of marks=N+1, where N represents the number of non-negligible interferents). The marks are defined as certain peak indices of moisture or/and interferent(s). For example, one mark is set at an $H_2O$ peak, while the other marks may be placed at the more pronounced peaks of major interferent constituents) of the process gas. The Y values are subscripted with their respective mark numbers. For pre-calibration data, these Y values are denoted with a prime ('). For calibration and normal operation, the notation will be without a prime sign.

Next, ratio functions are then defined and equations are gathered using the marked spectral data (block 106). A set of N ratio functions is determined for each interferent. Each of the ratio functions represents a ratio of the Y value of the interferent at a mark to the Y value of the same interferent at a mark chosen as a reference.

Next, a system of (N+1)-variable linear equations can be gathered for dried process gas and/or actual process gas, utilizing the ratio functions. At each mark, there is an equation equating the Y value of dried or actual process gas to the sum of the Y values of all spectrally non-negligible species in the process gas, including moisture and the interferents, at the pre-defined X value (index).

The system of (N+1) equations can then be solved for (N+1) unknowns, i.e., the Y values at the reference mark(s) of moisture and the N interferents, knowing the ratio function values computed from the spectral data collected at block 102, as well as the Y values of process gas mixture at all the marks through measurement (block 108). The concentrations of moisture and interferents in the process gas can then be inferred from the disentangled Y values and calibration data.

Figure 6:
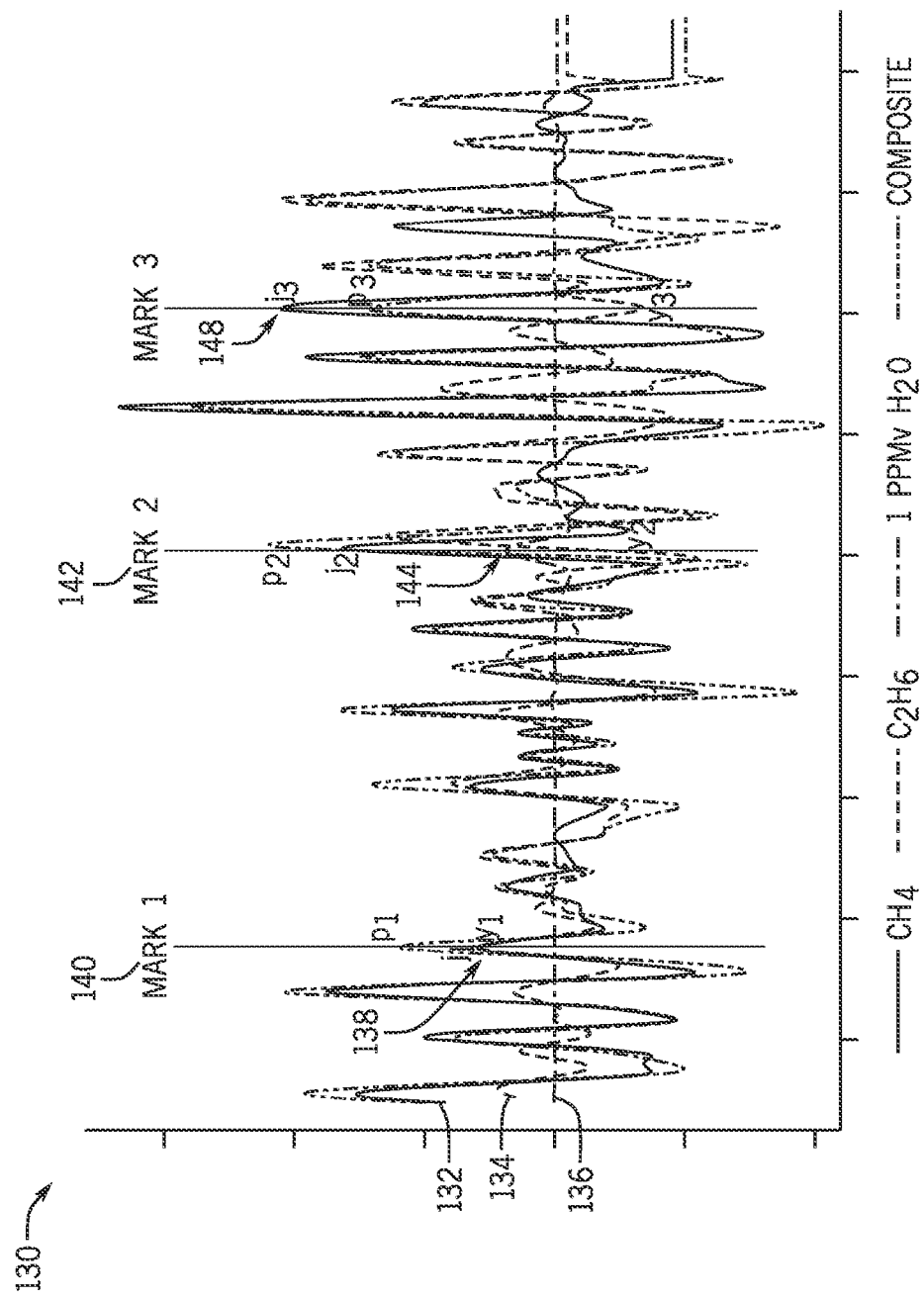
FIG. 6 is a diagram illustrating the spectral data of a gas sample containing moisture ($H_2O$) and two interferents (e.g., $CH_4$ and $C_2H_6$), in accordance with an embodiment.

Having now discussed the basic process of the logic 56, the discussion now turns to two exemplary application cases for the logic 56. FIG. 6 illustrates the spectral data 130 of a gas sample containing moisture ($H_2O$) and two interferents (e.g., $CH_4$ and $C_2H_6$). The logic 56 involving two interferents is readily applicable to liquefied natural gas (LNG) and hydrogen recycling applications, where $CH_4$ and $C_2H_6$ are the two main interferents spectrally interfering with moisture analysis while the other species are either transparent or non-interfering.

As mentioned above, spectra of moisture and each of the interferents are recorded in a non-interfering gas (e.g., $N_2$), at different pressures, e.g., 2.2, 2.5, and 2.8 PSIa, logging pressure and temperature data among other things. The concentrations of the interferents (i.e., $X'_{CH_4}$ and $X'_{C_2H_6}$) should reflect the concentrations found in the actual process gas. In some embodiments, multiple spectra results are collected and averaged to improve accuracy.

In FIG. 6, line 132 represents the $CH_4$ spectrum, line 134 represents the $C_2H_6$ spectrum, and line 136 represents the spectrum of $H_2O$. Line 140 represents the mixed process gas (e.g., containing the $CH_4$, $C_2H_6$, and $H_2O$) spectrum. As illustrated, the targeted $H_2O$ peak 144 is interfered by the neighboring $CH_4$ and $C_2H_6$ features, and therefore, moisture analysis may be impacted by any variation in gas composition. Accordingly, the variable gas compensation logic 56 may be used to achieve a more reliable moisture analysis and/or $CH_4$ and/or $C_2H_6$ analysis.

Next, the marks are defined, as discussed above. The signal magnitude (Y value) at a certain index (X value) is represented by j for CH4, by y for C2H6, by s for H2O, and by p for composite. There are 3 marks, each with a certain index (e.g., laser dependent). As illustrated, the CH4 peak 138 defines the index of "Mark 1" 140. The index of "Mark 2" 142 is defined as that of the H2O peak 144. The index of "Mark 3" 146 is defined as that of the other CH4 peak 148. The Y values are subscripted with their respective mark numbers. For pre-calibration data, these Y values are denoted with a prime ('). For calibration and normal operation, the notation will be without a prime sign.

Next, the ratio functions are determined. For each of the interferents, there are two ratio functions useful for the logic 56. The first ratio function is the ratio of the signal magnitude of the interferent at "Mark 2" to the signal magnitude of the interferent at "Mark 1". The second ration function is the ratio of the signal magnitude of the interferent at "Mark 3" to the signal magnitude at "Mark 1."

In the current example, there are two ratio functions defined with $CH_4$ spectrum:

$$R_{j21} = j'_2/j'_1, \text{ and}$$

$$R_{131} = j'_3/j'_1.$$

There are also two ratio functions defined with $C_2H_6$ spectrum:

$$R_{y21} = y'_2/y'_1, \text{ and}$$

$$R_{y31} = y'_3/y'_1.$$

Next, the following equations can be gathered for dry process gases and/or non-dry process gases.

With dried process gas, the following equations can be gathered:

At Mark 1, $p_1 = j_1 + y_1$;

At Mark 2, $p_2 = j_2 + y_2 = R_{j21} \cdot j_1 + R_{y21} \cdot y_1 + z$; and

At Mark 3, $p_3 = j_3 + y_3 = R_{j31} \cdot j_1 + R_{y31} \cdot y_1$

In the above three equations, $j_1$, $y_1$, and $z$ can be solved with the known ratio functions and with the measurements of $p_1$, $p_2$, and $p_3$. Here $z$ is defined as a residual error. The following analytical solutions can be directly used for coding:

$$j_1 = \frac{R_{y31} \cdot p_1 - p_3}{R_{y31} - R_{j31}};$$

$$y_1 = \frac{p_3 - R_{j31} \cdot p_1}{R_{y31} - R_{j31}}; \text{ and}$$

$$z = p_2 - R_{j21} \cdot j_1 - R_{y21} \cdot y_1.$$

With actual process gas, the following equations can be gathered:

At Mark 1, $p_1 = j_1 + y_1$;

At Mark 2, $p_2 = R_{j21} \cdot j_1 + R_{y21} \cdot y_2 + z + s$; and

At Mark 3, $p_3 = R_{j31} \cdot j_1 + R_{y31} \cdot y_1$.

In the above three equations, s (the true $H_2O$ peak value), $j_1$, and $y_1$ can be solved with the known values of z and ratio functions and with the measurements of $p_1$, $p_2$, and $p_3$. The following analytical solutions can be directly used for coding:

$$j_1 = \frac{R_{y31} \cdot p_1 - p_3}{R_{y31} - R_{j31}};$$

$$y_1 = \frac{p_3 - R_{j31} \cdot p_1}{R_{y31} - R_{j31}}; \text{ and}$$

$$s = p_2 - z - R_{j21} \cdot j_1 - R_{y21} \cdot y_1.$$

Accordingly, a more precise measurement of moisture may be obtained, taking into account the effects of the interferent gases.

Pressure and temperature may also have an effect on moisture analysis. In some embodiments, pressure and temperature compensation of true $H_2O$ peak value may be provided. For example, in some embodiments, after determining the true $H_2O$ peak value, s, pressure and temperature compensation is provided as follows:

CompensatedPeakValue=$s/C(P,T)$, where C(P,T) is a function of sample pressure and temperature, reflecting how the monitored $H_2O$ peak is affected by spectral broadening by the background gas (i.e., the process gas minus moisture).

In addition to enhanced moisture analysis, the logic 56 may be useful for measuring concentration of the interferents. In other words, the analyzer 10 may act as a multi-gas analyzer. In the current example, the analyzer 10, if so desired, could be used to detect CH4 and C2H6 at the same time as it detects H2O, at no extra material cost. In one embodiment, the spectral data collected in block 102 of FIG. 5 serve as a one-point calibration for interferents. In the current example, the detected concentrations for the interferents may be represented as follows:

$$\text{For } CH_4, X_{CH_4} = \frac{X'_{CH_4}}{j'_1} \cdot j_1 \cdot f_j(P); \text{ and}$$

$$\text{For } C_2H_6, X_{C_2H_6} = \frac{X'_{C_2H_6}}{y'_1} \cdot y_1 \cdot f_y(P).$$

The pressure compensation functions $f_j(P)$ and $f_y(P)$ are derived from the multiple-pressure spectral data collected in block 102 of FIG. 5. The pressure compensation function may be represented as $f(P)=f_0+f_1 \cdot P+f_2 \cdot P^2$. Depending on accuracy specification, more elaborate calibration, and pressure and temperature compensation can be implemented to refine accuracy on $CH_4$ and $C_2H_6$.

The logic 56 involving two interferents is readily applicable to liquefied natural gas (LNG) and hydrogen recycling applications, where $CH_4$ and $C_2H_6$ are the two main interferents spectrally interfering with moisture analysis while the other species are either transparent or non-interfering.

Further, the same principle used in the logic 56 of FIG. 6 can be applied to many other applications involving at least one interferent, with reduction for fewer interferent(s), expansion for more interferents.

FIG. 7 illustrates one such expansion. In FIG. 7, the spectral data 160 represents a cracked gas mixture typically having $CH_4$, $C_2H_4$, and $C_2H_6$ in relatively high percentages, $C_2H_2$ and $C_3H_6$ in relatively low percentage, and trace level moisture ($H_2O$).

As described above, spectra for the spectrally non-negligible constituents are collected at concentrations $X'_{CH_4}$, $X'_{C_2H_4}$, and $X'_{C_2H_6}$, respectively, in a non-interfering gas such as $N_2$, at different pressures. Line 162 represents spectrum of $H_2O$, line 164 represents spectrum of $CH_4$, line 166 represents spectrum of $C_2H_2$, line 168 represents spectrum of $C_2H_4$, line 170 represents spectrum of $C_2H_6$, line 172 represents spectrum of $C_3H_6$, and line 174 represents the "composite" spectrum of a cracked gas mixture from a steam cracker.

The signal magnitude (Y value) at a certain index (X value) is represented by x for $C_2H_4$, by j for $CH_4$, by y for $C_2H_6$, by s for $H_2O$, and by p for composite. The other species such as $C_2H_2$ and $C_3H_6$ in low percentage pose little interference, at a level that is negligible. Accordingly, in some embodiments, the logic 56 may disregard these minor species of negligible interference.

As discussed in FIGS. 5 and 6, the marks are defined. Because there are three interferents to be considered by the logic 56, there are 4 marks, each with a certain index. As illustrated, the index of "Mark 1" 176 is defined as that of the $C_2H_4$ peak 178, the index of "Mark 2" 180 as that of the $H_2O$ peak 182, the index of "Mark 3" 184 as that of the $CH_4$ peak 186, and the index of "Mark 4" 188 as that of the other $C_2H_4$ peak 190. The Y values are subscripted with their respective mark numbers. For pre-calibration data, these Y values are denoted with a prime ('). For calibration and normal operation, the notation will be without a prime sign.

Next, the ratio functions are defined. Because there are three interferents, three sets of corresponding ratio functions are defined as follows:

There are three ratio functions defined with $C_2H_4$ spectrum:

$$R_{x21}=x'_2/x'_1,$$

$$R_{x31}=x'_3/x'_1, \text{ and}$$

$$R_{x41}=x'_4/x'_1.$$

There are three ratio functions defined with $CH_4$ spectrum:

$$R_{j14}=j'_1/j'_4,$$

$$R_{j24}=j'_2/j'_4, \text{ and}$$

$$R_{j34}=j'_3/j'_4.$$

There are three ratio functions defined with $C_2H_6$ spectrum:

$$R_{y14}=y'_1/y'_4,$$

$$R_{y24}=y'_2/y'_4, \text{ and}$$

$$R_{y34}=y'_3/y'_4.$$

Next, equations are gathered for dried process gas, as follows:

$$\text{At Mark 1, } p_1=x_1+R_{j14} \cdot j_4+R_{y14} \cdot y_4;$$

$$\text{At Mark 2, } p_2=R_{x21} \cdot x_1+R_{j24} \cdot j_4+R_{y24} \cdot y_4+z;$$

$$\text{At Mark 3, } p_3=R_{x31} \cdot x_1+R_{j34} \cdot j_4+R_{y34} \cdot y_4; \text{ and}$$

$$\text{At Mark 4, } p_4=R_{x41} \cdot x_1+j_4+y_4.$$

In the above four equations, $x_1$, $j_4$, $y_4$, and z can be solved with the known ratio functions and the measurements of $p_1$, $p_2$, $p_3$, and $p_4$. Here z is defined as a residual error. For coding purpose, analytical solutions can be derived and used.

With actual process gas, the following equations can be gathered:

$$\text{At Mark 1, } p_1=x_1+R_{j14} \cdot j_4+R_{y14} \cdot y_4;$$

$$\text{At Mark 2, } p_2=s+R_{x21} \cdot x_1+R_{j24} \cdot j_4+R_{y24} \cdot y_4+z;$$

$$\text{At Mark 3, } p_3=R_{x31} \cdot x_1+R_{j34} \cdot j_4+R_{y34} \cdot y_4; \text{ and}$$

$$\text{At Mark 4, } p_4=R_{x41} \cdot x_1+j_4+y_4.$$

In the above four equations, s, $x_1$, $j_4$, and $y_4$ can be solved with the known values of z and ratio functions and with the measurements of $p_1$, $p_2$, $p_3$, and $p_4$. For coding purpose, analytical solutions can be derived and used.

In some embodiments, pressure and temperature compensation of true $H_2O$ peak value may be provided. For example, in some embodiments, after determining the true $H_2O$ peak value, s, pressure and temperature compensation is provided as follows:

$$\text{CompensatedPeakValue}=s/C(P,T),$$

where C(P,T) is a function of sample pressure and temperature, reflecting how the monitored $H_2O$ peak is affected by spectral broadening by the background gas.

In addition to enhanced moisture analysis, the logic 56 may be useful for measuring concentration of the interferents. In other words, the analyzer 10 may act as a multi-gas analyzer. In the current example, the analyzer 10, if so desired, could be used to detect $C_2H_4$, $CH_4$, and $C_2H_6$ at the same time as it detects $H_2O$, at no extra material cost. In one embodiment, the spectral data collected in block 102 of FIG. 5 serve as a one-point calibration for interferents. In the current example, the detected concentrations for the interferents may be represented as follows:

$$\text{For } C_2H_4, X_{C_2H_4} = \frac{X'_{C_2H_4}}{x'_1} \cdot x_1 \cdot f_x(P);$$

$$\text{For } CH_4, X_{CH_4} = \frac{X'_{CH_4}}{j'_1} \cdot j_1 \cdot f_j(P); \text{ and}$$

$$\text{For } C_2H_6, X_{C_2H_6} = \frac{X'_{C_2H_6}}{y'_1} \cdot y_1 \cdot f_y(P).$$

The pressure compensation functions $f_x(P)$, $f_j(P)$, and $f_y(P)$ are derived from the multiple-pressure spectral data collected in block 102 of FIG. 5. The pressure compensation function may be represented as $f(P)=f_0+f_1\cdot P+f_2\cdot P^2$. Depending on accuracy specification, more elaborate calibration, and pressure and temperature compensation can be implemented to refine accuracy on $CH_4$ and $C_2H_4$ and $C_2H_6$.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
an analyzer configured to detect moisture, or interferent(s), or both, in a process gas, wherein the analyzer comprises:
an absorption cell enclosing and conducting the process gas;
a pressure control device configured to reduce a pressure of the process gas inside the absorption cell to provide de-pressurized process gas sample at a pressure lower than an ambient pressure of the process gas;
a light emitting device configured to transmit light through the de-pressurized process gas inside the absorption cell;
a photodetector configured to detect an intensity of the light transmitted through the de-pressurized process gas and exiting the absorption cell; and
electronic circuitry configured to detect moisture, or one or more interferents, or both, in the process gas, using variable gas compensation logic, wherein the variable gas compensation logic is configured to compensate moisture detection for the interferents utilizing one or more X values associated with certain absorption features of the interferents and one or more ratio functions of the interferents, wherein the one or more ratio functions are defined as a ratio of Y values at two different marks within the spectrum of each interferents, and wherein a first Y value at a first mark relates to an interferent and a second Y value at a second mark relates to a reference mark for the same interferent.

2. The system of claim 1, wherein the absorption cell comprises a multipass absorption cell.

3. The system of claim 1, wherein electronic circuitry configured to:
acquire and process at least one spectrum of each of the one or more intereferents, moisture, and the process gas;
store the one or more ratio functions of the interferents that are defined based upon the spectra of the interferents and moisture; and
utilize the ratio functions to compensate for any cross interference from the one or more interferents.

4. The system of claim 3, wherein the electronic circuitry is further configured to:
store calibration data for moisture, one or more interferents, or both; and
determine a concentration of moisture, a concentration of at least one of the interferents, or both, in the process gas based at least on the spectrum of the process gas and the calibration data.

5. The system of claim 4, wherein the electronic circuitry is further configured to provide compensation for pressure, temperature, or both, of the process gas sample.

6. The system of claim 1, wherein the process gas is of constant, or variable, chemical composition.

7. The system of claim 1, wherein the process gas is pipeline natural gas, liquefied natural gas (LNG) feed gas, regasified LNG, cracked gas out of a steam cracker, polyethylene feedstock, or hydrogen recycle gas.

8. The system of claim 1, wherein the light emitting device comprises a laser, a diode laser, or a quantum cascade laser.

9. The system of claim 1, wherein electronic circuitry is configured to facilitate direct absorption spectroscopy, derivative spectroscopy, or cavity ring down spectroscopy.

10. The system of claim 1, wherein the pressure control device comprises a vacuum pump or an aspirator.

11. The system of claim 8, wherein the diode laser comprises:
a thermoelectric cooler;
a temperature sensor; and
a built-in photodetector configured to detect an intensity of backward emission from the diode laser.

12. A method for detecting moisture, one or more interferents, or both, compensating for a variation in chemical composition, pressure, temperature, or a combination thereof, of a process gas, comprising:
reducing, with a pressure control device, a pressure of the process gas inside an absorption cell enclosing and conducting the process gas to provide a de-pressurized process gas at a pressure lower than an ambient pressure of the process gas;
collecting, with a spectral analyzer, one or more spectra of the de-pressurized process gas, and its light-absorbing constituents including moisture and one or more of the interferents;
defining marks at certain X values in accordance with certain absorption features of moisture or the interferents on the spectral analyzer;
determining one or more ratio functions that are defined as a ratio of Y values at two different marks within the spectrum of each interferents, wherein a first Y value at a first mark relates to an interferent and a second Y value at a second mark relates to a reference mark for the same interferent;

utilizing the determined ratio functions to disentangle the spectral interference between the moisture and the interferents, present in the spectrum of the de-pressurized process gas, to compute the Y values attributing to moisture and the interferents, wherein the Y values represent signal magnitude; and determining, with the spectral analyzer, at least one concentration of the moisture, the one or more interferents, or a combination thereof.

13. The method of claim 12, wherein an interferent is $CH_4$, $C_2H_2$, CAL, $C_2H_6$, or $C_3H_6$.

14. The method of claim 12, comprising: recording the spectra of the interferents, in a non-interfering gas, at a concentration reflecting that present in the process gas, at more than one pressure.

15. The method of claim 14, wherein the spectra of the interferents provide a one-point calibration for quantifying concentrations of the interferents with compensation for pressure, temperature, or both.

16. The method of claim 12, wherein the disentanglement of spectral interference is achieved by solving a system of linear equations incorporating the ratio functions.

17. The method of claim 12, wherein the moisture analysis comprises compensation for pressure, temperature, or both, of the process gas sample, accounting for spectral broadening effects by both interfering and non-interfering constituents.

18. A tangible, non-transitory, machine-readable medium, comprising machine-readable instructions to:
receive, from a spectral analyzer, one or more spectra of a de-pressurized process gas, and its light-absorbing constituents including moisture and one or more of the interferents, wherein a pressure control device reduces a pressure of a process gas inside an absorption cell enclosing the process gas to generate the de-pressurized process gas, and wherein the pressure of the de-pressurized process gas is lower than an ambient pressure of a sample gas;

define, via a processor, marks at certain X values of the one or more spectra of the de-pressurized process gas and its light-absorbing constituents in accordance with certain absorption features of moisture or the interferents on the spectral analyzer;

determine, via the processor, one or more ratio functions that are defined as a ratio of Y values at two different marks within the spectrum of each interferent, wherein a first Y value at a first mark relates to an interferent and a second Y value at a second mark relates to a reference mark for the same interferent; and utilize, via the processor, the determined ratio functions to disentangle the spectral interference between the moisture and the interferents, present in the spectrum of the de-pressurized process gas, to compute the Y values attributing to moisture and the interferents, wherein the Y values represent signal magnitude.

19. The machine-readable medium of claim 18, comprising instructions to:
record the spectra of the interferents, in a non-interfering gas, at a concentration reflecting that present in the process gas, at more than one pressure.

20. The machine-readable medium of claim 18, comprising instructions to:
solve a system of linear equations incorporating the ratio functions to compute the Y values attributing to moisture and the interferents.

\* \* \* \* \*